US011179287B1

(12) United States Patent
Mirbahaeddin

(10) Patent No.: US 11,179,287 B1
(45) Date of Patent: Nov. 23, 2021

(54) PROTECTIVE SHIELD SYSTEM

(71) Applicant: Majid Mirbahaeddin, Carrollton, TX (US)

(72) Inventor: Majid Mirbahaeddin, Carrollton, TX (US)

( * ) Notice: Subject to any disclaimer, the term of this patent is extended or adjusted under 35 U.S.C. 154(b) by 36 days.

(21) Appl. No.: 16/902,092

(22) Filed: Jun. 15, 2020

(51) Int. Cl.
*A61G 15/10* (2006.01)
*A47C 7/62* (2006.01)
*A61G 13/10* (2006.01)
*A61M 16/00* (2006.01)
*A61C 17/02* (2006.01)

(52) U.S. Cl.
CPC ............. *A61G 15/10* (2013.01); *A47C 7/62* (2013.01); *A61C 17/0208* (2013.01); *A61G 13/108* (2013.01); *A61M 16/009* (2013.01)

(58) Field of Classification Search
CPC . A62B 17/006; A62B 17/04; A62B 18/00–10; A62B 17/08; A42B 3/28–288; A47C 7/62; A61M 16/0087–009; A61M 16/0627; A61M 16/01; A61G 15/00–18; A61G 10/04; Y10S 128/91; A41D 13/11
USPC .... 128/205.27, 910, 203.12; 433/25, 91–96; 454/49, 188–193
See application file for complete search history.

(56) References Cited

U.S. PATENT DOCUMENTS

| | | | |
|---|---|---|---|
| 3,635,522 A * | 1/1972 | Kerwit | A47C 7/68 297/153 |
| 3,877,691 A * | 4/1975 | Foster | A61M 16/0627 5/600 |
| 4,055,173 A * | 10/1977 | Knab | A41D 13/1153 128/847 |
| 5,715,813 A * | 2/1998 | Guevrekian | A61M 16/009 128/205.12 |
| 6,691,314 B1* | 2/2004 | Grilliot | A62B 17/04 128/201.25 |
| 2013/0306060 A1* | 11/2013 | Cota | A61M 15/00 128/200.14 |
| 2014/0366890 A1* | 12/2014 | Tao | A61M 16/009 128/849 |
| 2015/0238264 A1* | 8/2015 | Kerns | A61B 46/23 128/852 |
| 2017/0007796 A1* | 1/2017 | Pedro | A61B 5/082 |

(Continued)

OTHER PUBLICATIONS

Merriam-Webster, Definition of Pipe, Accessed Aug. 31, 2020, https://www.merriam-webster.com/dictionary/pipe (Year: 2020).*

(Continued)

*Primary Examiner* — Elliot S Ruddie
(74) *Attorney, Agent, or Firm* — Perkins Coie LLP

(57) ABSTRACT

Methods, apparatus, and systems for reducing transmission of aerosol droplets in a medical or dental procedure are described. One protective shield system includes a base plate, a shield having at least one transparent section, and a pipe or conduit comprising a plurality of holes thereon. The shield is configured to be removably attached to the base plate to allow attachment of the shield to the base plate prior to the medical or dental procedure and removal of the shield from the base plate after the medical or dental procedure. The pipe or conduit is positioned adjacent to an inner surface of the shield and on at least part of a perimeter of the shield. The pipe includes an end that is configured to connect to a suction system to enable removal of the aerosolized particles from below the shield during the medical or dental procedure.

29 Claims, 9 Drawing Sheets

(56) References Cited

U.S. PATENT DOCUMENTS

2018/0132550 A1* 5/2018 Czajka ................ A62B 18/045
2020/0016774 A1* 1/2020 Keen ................ F16M 11/2064

OTHER PUBLICATIONS

MacMillan Dictionary, "platform", https://www.macmillandictionary.com/dictionary/american/platform#platform_14; accessed Dec. 17, 2020 (Year: 2020).*

Aegis Aerosol VacStation, CAO Group Inc., available at address: https://caogroup.com/products/aegis-aerosol-vacstation#.

* cited by examiner

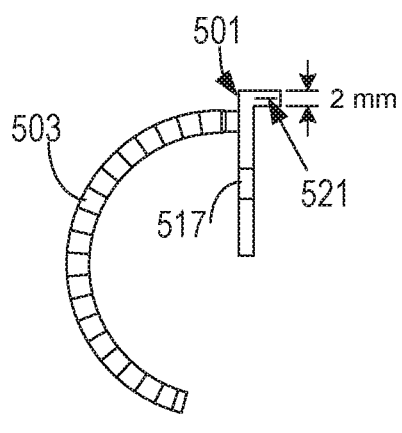
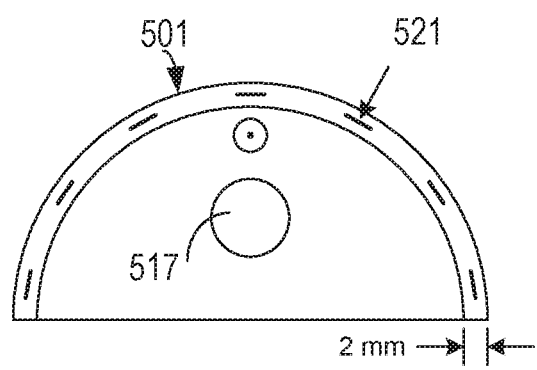
FIG. 5A     FIG. 5B
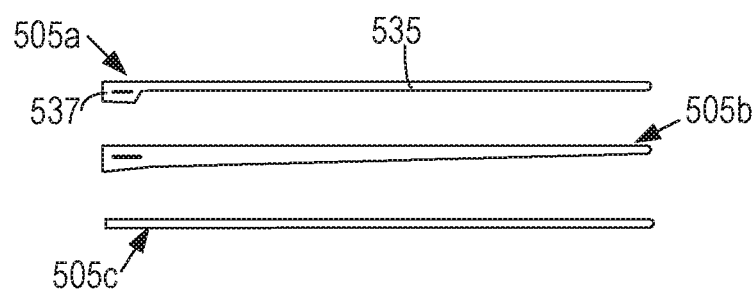
FIG. 5C
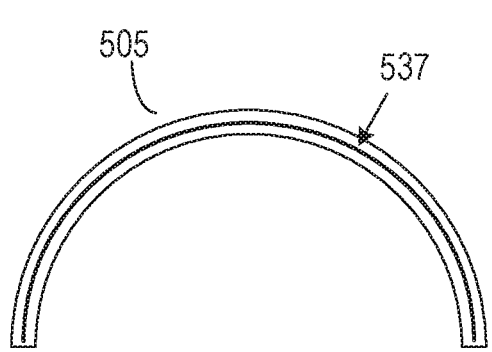
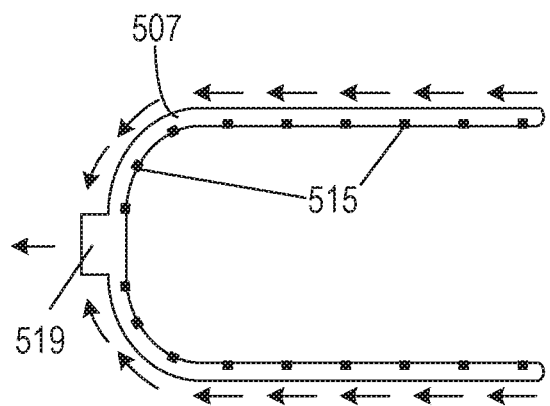
FIG. 5D     FIG. 5E

PROTECTIVE SHIELD SYSTEM

BACKGROUND

A communicable disease is one that is spread from one person to another through a variety of ways, such as contact with blood and bodily fluids or breathing in aerosolized particles carrying viruses. From the coronavirus-based diseases, including coronavirus disease-2019 (COVID-19), to influenza, Lyme disease malaria and Ebola, outbreaks of infectious diseases can have an extraordinary impact on human health. Preventing and controlling the spread of disease is at the heart of much public health work.

BRIEF DESCRIPTION OF THE DRAWINGS

FIG. 5A illustrates a side view a back plate in accordance with one or more embodiments of the present technology.

FIG. 5B illustrates a front view the back plate shown in FIG. 5A in accordance with one or more embodiments of the present technology.

FIG. 5C cross-sectional views of three example shields in accordance with one or more embodiments of the present technology.

FIG. 5D illustrates another view of an example shield in a bent configuration in accordance with one or more embodiments of the present technology.

FIG. 5E illustrates a top view of a vacuum pipe in accordance with one or more embodiments of the present technology.

DETAILED DESCRIPTION

Figure 1:
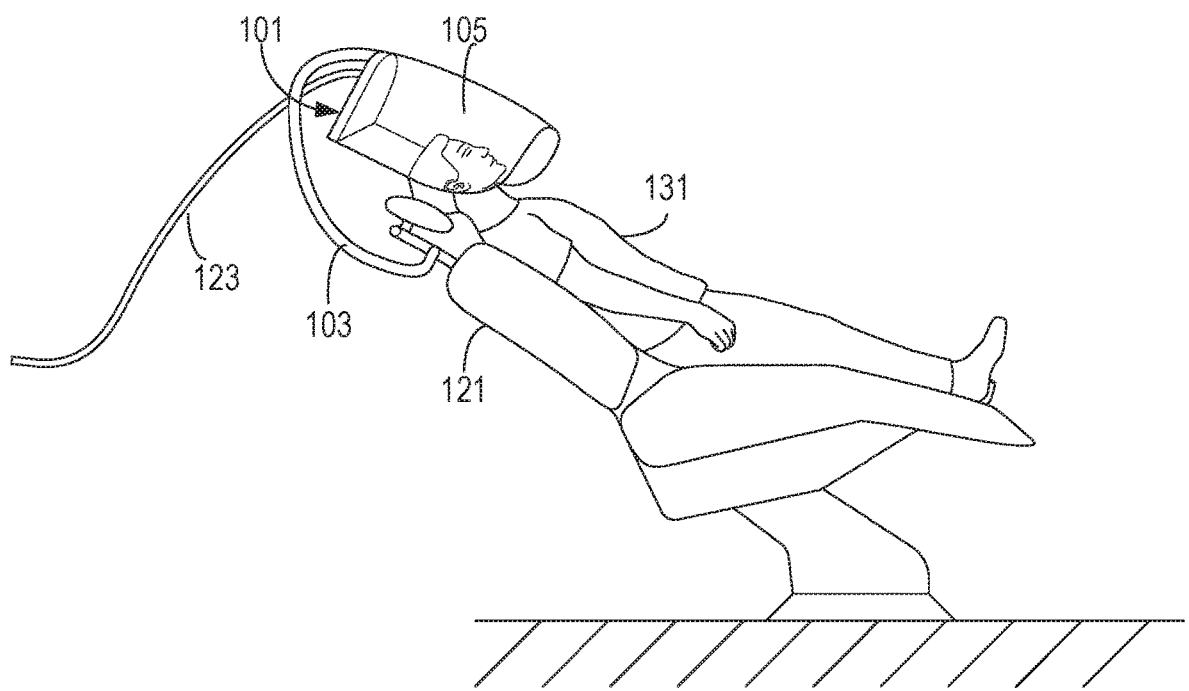
FIG. 1 illustrates an example configuration of a protective shield system used in a medical or dental procedure in accordance with one or more embodiments of the present technology

Communicable diseases pose risks to societies in a variety of ways. The recent COVID-19 pandemic has brought enormous amount of challenges to communities and healthcare professionals. In response to the COVID-19 pandemic, Centers for Disease Control and Prevention (CDC) recognizes the need to provide necessary healthcare services while minimizing risk to patients and healthcare personnel. CDC has developed a framework for healthcare personnel and healthcare systems for delivery of care during the pandemic, including the use of personal protection equipment (PPE). Similarly, guidelines have been issued for dental health care, which is also an integral part of the public health framework. Health and dental care professionals should wear a surgical mask, eye protection, and a gown or protective clothing during procedures likely to generate splashing or spattering of blood or other body fluids. Healthcare facilities must ensure that any reusable PPE is properly cleaned, decontaminated, and maintained after and between uses.

While the use of PPE increases the level of protection for healthcare professionals, it alone may not provide optimal protection. For example, performing aerosol-generating procedures on patients requires a higher level of protection for healthcare professionals. Currently, the CDC recommends the use of N95 respirators or other disposable filtering facepiece respirators, if available. However, such respirators should be used in the context of a respiratory protection program, which includes medical evaluations, training, and fit testing. Should a respirator become loose during or between procedures, a healthcare professional can be exposed to the virus and the risk of spreading the disease to subsequent patients is also increased.

Additionally, while the use of PPEs may provide some protection for the medical service providers, they do not mitigate the spread of aerosolized particles that are produced during the dental or oral surgery procedures and are spread from the patient to the surrounding premises.

This patent document discloses methods, devices and systems related to protective shield systems that provide an increased level of protection for the healthcare professionals and their patients in aerosol-generating procedures, including but not limited to any dental procedures ranging from root canals, to dental implants to routine dental cleaning procedures, as well as oral and maxillofacial Surgical procedures. The disclosed protective shield systems do not require additional training or fit testing and provide protection for both the dental health professional and the patient by reducing or eliminating the spread of aerosolized particulates and removing any such particulates rapidly and effectively. The disclosed protective shield systems are easy to use and can be manufactured and assembled in a cost effective manner, can be implemented as stand-alone systems, or can be readily adapted for use with existing fixtures, such as dental chairs and vacuum suction systems that already exist as part of the dental suite. Components of the disclosed protective shield systems can be easily replaced or sanitized between procedures to minimize and/or eliminate the risk of transmitting communicable diseases from patients to healthcare professionals, from healthcare professionals to subsequent patents, and from patients to patents.

FIG. 1 illustrates an example configuration of a protective shield system 100 used in a medical or dental procedure in accordance with one or more embodiments of the present technology. The system 100 includes a base plate 101 that is coupled to an operating platform 121, such as a dental chair or an operating bed. In some embodiments, the protective shield system 100 includes a support arm 103 (e.g., a flexible arm or a mounting arm) that is coupled to the base plate. The support arm 103 allows the base plate to be positioned flexibly with respect to the patient 131 and enable the face shield position to be adjusted. For example, in a dental procedure such as shown in FIG. 1, the base plate is positioned in proximity to the patient's head. In other medical procedures in which the disclosed shield system may be implemented, the base plate can be positioned close to an operating area, such as a neck, a limb, or an abdomen of the patient 131. A healthcare professional can adjust the position and/or orientation of the base plate 101 using the support arm 103 prior to or during the procedure to ensure there is sufficient room to operate on the patient underneath the shield. In some embodiments, the support arm 103 is an integral part of the protective shield system 100. In some embodiments, the support arm 103 is provided separately from the protective shield system 100. For example, the support arm 103 can be disengaged from the backplate 101 to allow replacement, disposal and/or sterilization of the components of the protective shield system 100.

The protective shield system 100 also includes a shield 105 that includes at least one transparent area or section that allows the patient's mouth (or other desired area on patient's body) to be viewed by the medical practitioner. In some implementations, parts of the shield 105 may be translucent or opaque. The shield can be removably coupled to the base plate 101. During the procedure, the shield 105 prevents aerosol droplets and/or mists from splashing the healthcare professional. After the procedure is completed, the shield 105 can be removed from the base plate 101 so that it is either replaced (e.g., disposable shields) or sanitized (e.g., reusable shields) for subsequent procedures. The compartment or space underneath the transparent shield 105 is augmented by a vacuum or suction system. In some embodiments, a thin vacuum pipe (see, e.g., FIG. 4) that includes a plurality of holes is positioned under (e.g., around a perimeter of) the transparent shield 105. The thin vacuum pipe is coupled to a vacuum suction system via a hose or conduit 123 that is connected to an interface, such as a hole on the base plate 101, so that droplets or mist generated during the procedure can be drawn away through the holes.

Figure 2:
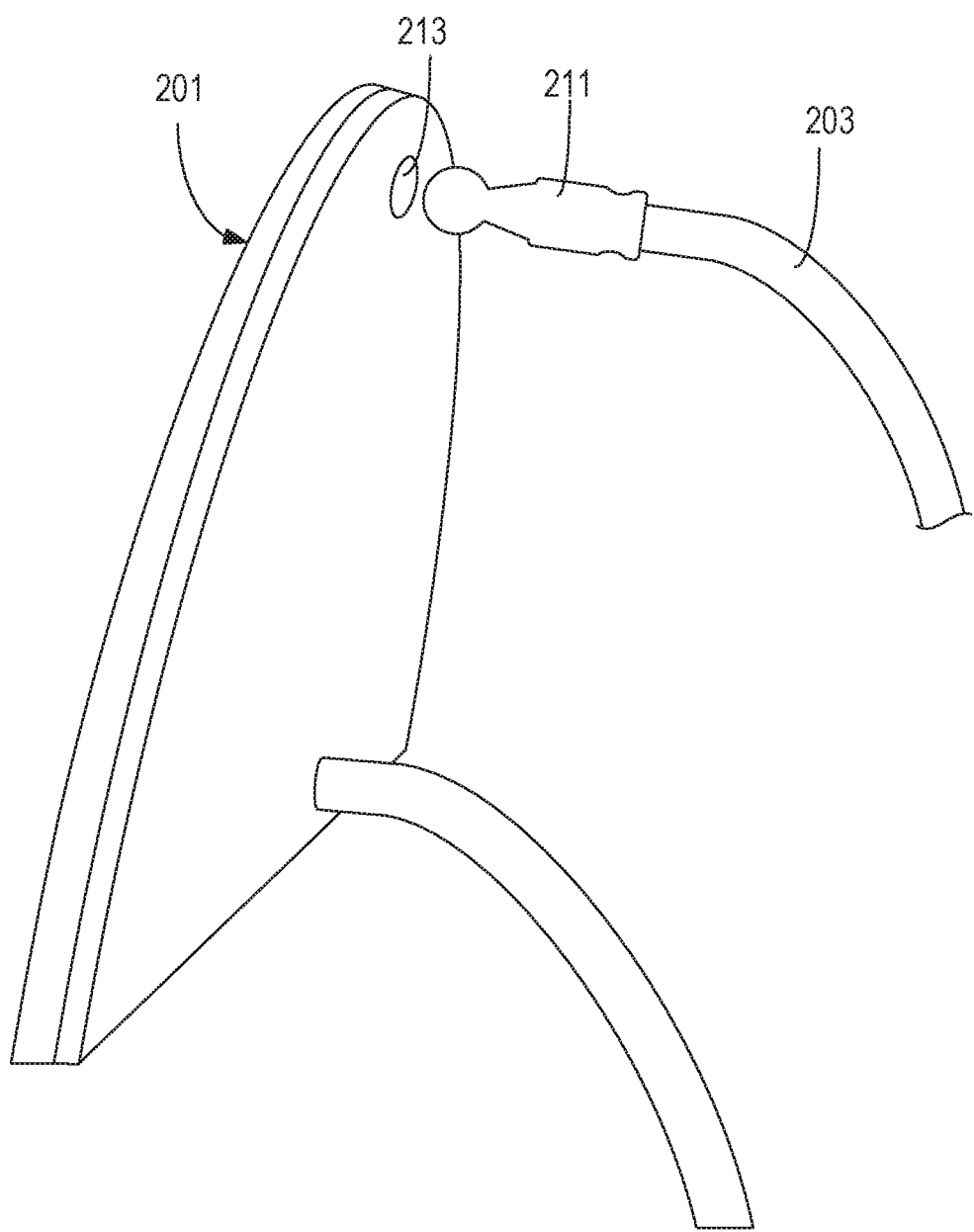
FIG. 2 illustrates an example of a coupling mechanism that couples a base plate and a supporting arm in accordance with one or more embodiments of the present technology.

One of the features of the disclosed protective shield systems is to provide flexible control of the protective shield system so that the base plate and transparent shield are positioned accurately to allow optimal protection of a healthcare professional while providing sufficient room for the operation. FIG. 2 illustrates an example of a coupling mechanism that allows a base plate and a supporting arm to be connected in accordance with one or more embodiments of the present technology. In this embodiment, the support arm 203 is a flexible arm that can be manipulated (e.g., twisted and/or bent) in different directions. One end of the flexible support arm 203 is connected to a stand or a clamp that is fastened to the back of an operating platform (e.g., a dental chair or an operating bed—see, e.g., FIG. 3). The other end of the flexible support arm 203 includes a coupling mechanism such as a male-end of a ball-and-socket of a rotating bracket 211. In the configuration of FIG. 2, the base plate 201 includes a cavity 213 as a female-end of the rotating bracket 211 (e.g., a socket). Once the bracket 211 and the cavity 213 are coupled together, they work seamlessly together to allow flexible control of the base plate's position and orientation. It should be noted that in the alternative other coupling mechanisms, including but not limited to a universal joint connector, can be used to allow the position of the backplate-shield assembly to be adjusted.

Figure 3:
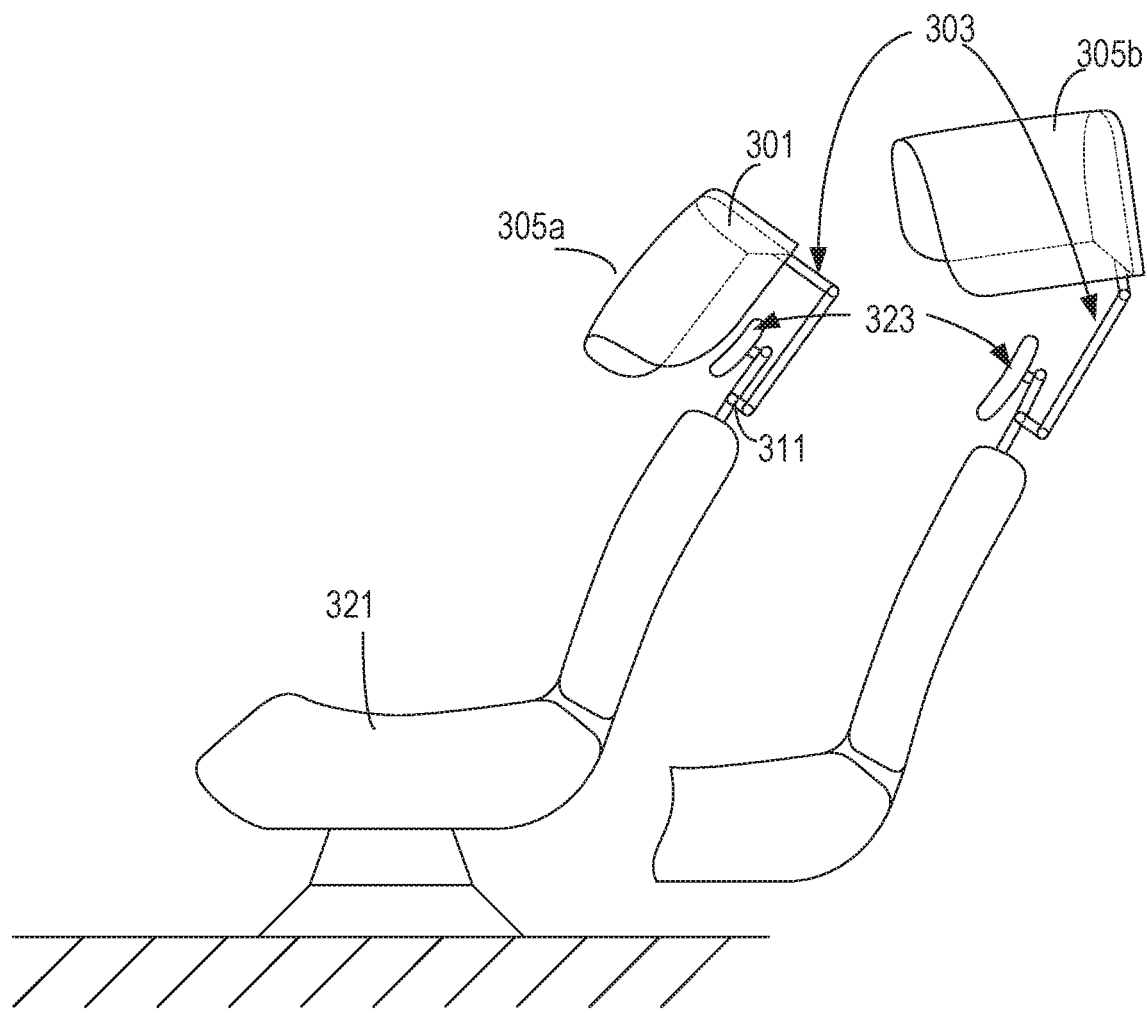
FIG. 3 illustrates another example configuration of a protective shield system in accordance with one or more embodiments of the present technology.

FIG. 3 illustrates another example configuration of a protective shield system in accordance with one or more embodiments of the present technology. In this example, the base plate 301 is coupled to the back of a dental chair 321 via a mounting arm 303. The mounting arm 303 includes a fastener 311, such as a clamp, that is fastened to a lower section of the headrest 323. The mounting arm 303 includes multiple sections that can be moved or rotated independently with respect to each other to provide flexible positioning of the base plate 301 and the shield. During the procedure, the shield can be moved to a "closed position" 305a so that it is positioned between the patient's head and the dentalcare professional to prevent aerosol droplets or mists from splashing to the dentalcare professional. The shield can be moved to an "open position" 305b to allow the patient to step off the dental chair or to a partially open position to, for example, allow repositioning of the patient's head. The shield can also be easily removed from the base plate 301 in the open position 305b so that it can be replaced or sanitized.

Figure 4:
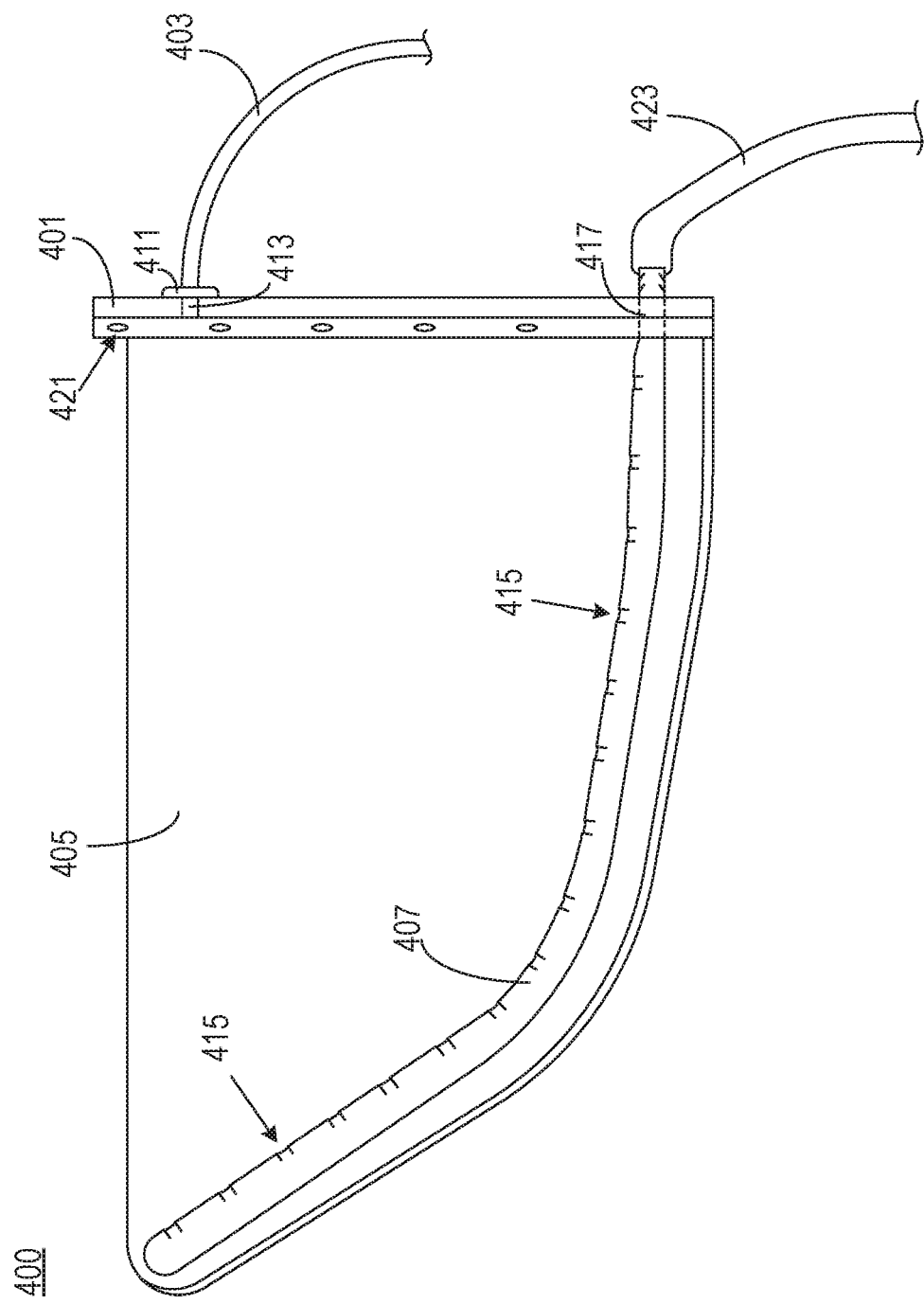
FIG. 4 illustrates a side view of an example protective shield system in accordance with one or more embodiments of the present technology.

FIG. 4 illustrates a side view of an example protective shield system 400 in accordance with one or more embodiments of the present technology. The protective shield system 400 includes a base plate 401. The base plate 401 includes an interface 413 (e.g., a female-end of a rotating bracket) that can be coupled to a positioning arm 403 (e.g., via a male-end of the rotating bracket 411). As described above, the positioning arm 403 can include a flexible structure that provides adjustable control of the position and/or the orientation of the base plate 401 with respective to the patient.

The protective shield system 400 also includes a shield 405 that is removably coupled to the base plate 401. The shield 405 can be entirely transparent, or have transparent sections (e.g., in the middle or the end thereof) that provides a clear line of sight for the medical practitioner to view the target area on the patient. The base plate 401 can be made of a smooth solid material (e.g., hard plastic) so that it can be easily sanitized (e.g., by spraying sanitizing mixture or by using sanitizing wipes) between procedures. In some embodiments, the base plate 401 includes one or more magnets 421 embedded along one side of the base plate. The shield 405 also includes one or more metallic strips, or alternatively, one or more magnets, embedded along an end of the shield so that the shield can be movably attached to the base plate 401. For example, when the end of the shield is brought to the proximity of the base plate 401, the magnetic attraction between the magnets and/or metallic strips facilitates secure connection of the shield and the base plate. In some embodiments, the base plate 401 includes a groove (not shown in FIG. 4). One side of the shield can slide through the groove to be removably attached to the base plate. Other coupling mechanisms that allow the shield to be removably coupled to the base plate can also be implemented.

The protective shield system 400 further includes a vacuum pipe 407 positioned around all or a portion of the perimeter of the shield 405. It should be noted that in this context, perimeter is used convey not just the geometrical perimeter of the shield, but also locations in the periphery of the central section of the shield and/or the areas surrounding the clear sections of the shield. In some embodiments, the vacuum pipe 407 is in contact with the shield 405 when the shield 405 is attached to the base plate 401. In some embodiments, an additional layer of padding (e.g., cotton or gauze) can be added to ensure that there is no gap between the shield 405 and the vacuum pipe 407 to prevent the aerosol droplets, mists, or condensation of the droplets/mists, to leak. The vacuum pipe 407 is connected to a vacuum suction system through a hose or a conduit 423 via an interface 417 (e.g., a hole) on the base plate 401 and/or associated connectors. A plurality of holes 415 distributed on the vacuum pipe 407 capture and draw the droplets or mist generated during the procedure. For example, during a dental procedure, mist, water or other types of droplets may accumulate on the shield 405. The holes 407, coupled to the vacuum or suction system, facilitate the removal of not only the air and aerosolized particles from under the shield 405, but also remove condensation that may be formed on the shield 405. For example, at least some of the holes 407 may be positioned to contact sections of the inner surface of the shield 405 to capture and remove condensation from the inner surface of the shield 405. This feature provides the added benefit of maintaining a clear view to the target area and avoiding fogging of the shield 405.

FIGS. 5A-5E illustrate additional details for an example protective shield system in accordance with one or more embodiments of the present technology. FIGS. 5A-5B illustrates a side view and a corresponding front view, respectively, of a back plate 501 without a shield attached to it. As noted earlier, after a procedure is completed, the shield can be removed for disposal or sanitization (e.g., by detaching the transparent shield from the magnet embedded at one side of the base plate). The vacuum pipe that is in contact with the transparent shield can be removed from the base plate and replaced as well. The base plate 501 remains attached to the supporting arm 503 and can be easily sanitized by various means, e.g., spraying sanitizing solutions onto the back plate or wiping the surface of the plate. The interface 517 (e.g., a hole) through which the vacuum pipe is connected to a vacuum or suction system can also be sanitized in a similar manner.

The shape of the base plate 501 can be adapted according to the types of procedures performed. For example, the base plate 501 can have a semicircular shape, such as sown in FIG. 5B. The semicircular-shaped base plates can be suitable for dental procedures. For medical procedures that operate on other parts of the body, e.g., a patient's abdomen, the base plate can have a larger dimension with a different curvature along one side. In some embodiments, the base plate can have an L-shaped side profile (e.g., as shown in FIG. 5A). The top section of the base plate 501 can have a thickness that ranges from, for example, 1 mm to 5 mm to provide sufficient room for the coupling mechanism (e.g., magnet, groove, etc.) to couple the shield. In the example shown in FIGS. 5A-5B, the top section of the base plate has a thickness of 2 mm. As mentioned above, in some embodiments, the coupling mechanism can use one or more magnets 521 embedded along at least one section of the base plate to enable easy coupling/decoupling of the transparent shield. In some embodiments, the base plate includes a thin groove to allow the shield to slide through and be attached to the base plate. It should be noted that for facilitating the description of the disclosed embodiments, the term base plate has been used to refer to the back section of the protective shield system that provides an interface for connecting the shield, attaching the support arm, and accommodating the vacuum connections. It is, however, understood that such a base plate may include one or more segments or sections configured to provide the needed interfaces or connections. Additionally, the term base plate does not necessarily refer to a flat plate, but can include non-flat features, such as curved surfaces or edges or angled sections or surfaces (see, e.g., FIG. 5A).

FIG. 5C illustrates cross-sectional views of three example shields in accordance with one or more embodiments of the present technology. A shield can be made of flexible materials that can bend or can be shaped according to the shape or curvature accommodated by the base plate. In one example, the shield 505a includes a first section 535 that has a uniform thickness and a second section 537 with embedded magnet(s) or metallic components to allow the shield to be removably attached to the base plate. In another example, the thickness of the shield 505b gradually increases from one end to the other end to provide space for embedding the magnet(s) or metallic components. In yet another example, the shield 505c has a uniform thickness. In this example, the shield 505c can attach to the base plate by sliding through a thin groove provided on the base plate.

FIG. 5D illustrates another view of an example shield in a bent configuration in accordance with one or more embodiments of the present technology. The shield is bent according to the curvature of one side of the base plate. In some embodiments, as shown in 5D, the shield 505 is bent to form a semicircle profile. The transparent shield 505 includes embedded magnet(s) or metallic components to allow the transparent shield to be removably attached to the base plate.

FIG. 5E illustrates a top view of a vacuum pipe 506 in accordance with one or more embodiments of the present technology. The vacuum pipe 507 includes an opening 519 that is coupled to the interface 517 of the base plate 501 for connection to a vacuum suction system (the arrows illustrate the direction of the air flow). The opening 519 can, for example, be part of a T-connector that can be used to deliver vacuum connectivity to the vacuum pipe 507 on both sides of the shield. The vacuum pipe 507 includes a plurality of holes 515 distributed uniformly or non-uniformly across the surface of the pipe. As noted earlier, the holes 515 may be facing in different directions to ensure proper removal of aerosolized particulates and condensation below the shield, as well as on the surface of the shield. The holes can have various shapes, such as round, square, rectangular and other shapes. Different distributions of the holes can be provided for different types of procedures to ensure that aerosol droplets and mist, and/or condensed droplets dripping from the transparent shield, are captured by the holes 515 and drawn by the vacuum suction system (as indicated by the arrows in FIG. 5E). The vacuum pipe 507 can be disposable so as to mitigate any concerns regarding sterilization of the vacuum pipe 807, which may have a small amount of fluid trapped therein. The vacuum pipe 507 can be made of degradable materials to reduce the impact on the environment.

It should be noted that other configurations of the vacuum pipe 507 can be implemented in accordance with the disclosed technology. For example, in some implementations, the density and/or size of holes 515 may be differ at different sections of the vacuum pipe 507 to accommodate a need for stronger or weaker vacuum suction and removal at different locations within the shield system. In some implementations, the layout of the vacuum pipe 505 may not be symmetrical so as to enable differing vacuum suction and removal capabilities at different locations within the shield system. In yet other implementations, the strength of vacuum suction and removal may be controlled via adjusting the vacuum/suction system itself. For example, the suction system can be configured to produce multiple levels of suction strengths. In some embodiments, the suction system provided in a dental suite is used to implement the vacuum system for the disclosed protective shield system. In such implementations, an end of an existing suction system can be adapted to be coupled to the protective shield system's vacuum hose or conduit. It should be further noted that the pipes or conduits disclosed herein need not have a circular cross-section. As such the disclosed protective shield systems can be implemented using pipes or conduits having other cross-sections, such as rectangular, square, triangular and irregular cross-sections, and be uniform or non-uniform throughout the length of the pipe or conduit.

Figure 6:
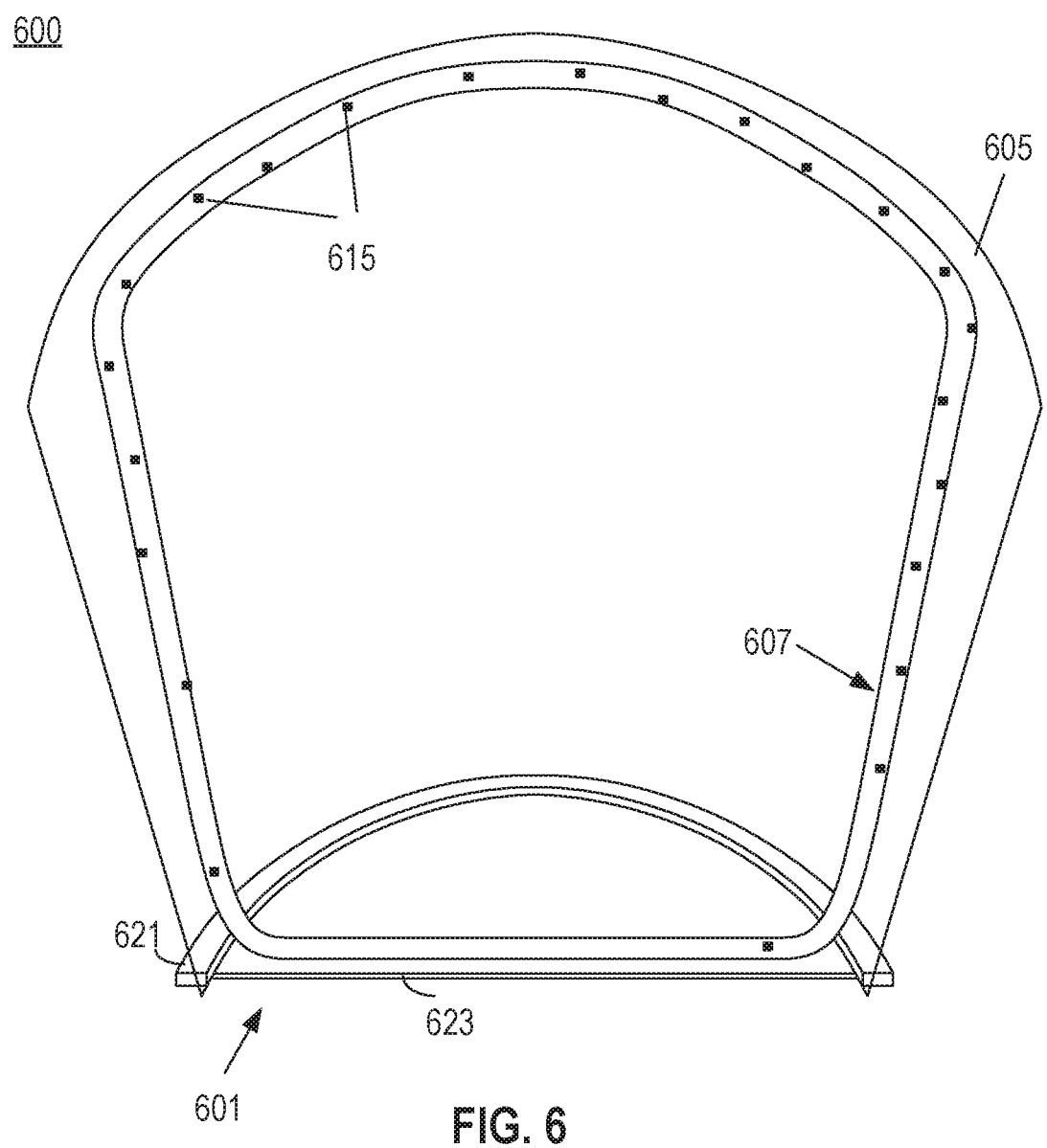
FIG. 6 illustrates yet another example protective shield system in accordance with one or more embodiments of the present technology.

FIG. 6 illustrates yet another example protective shield system 600 in accordance with one or more embodiments of the present technology. In this embodiment, the base plate 601 includes a thick cured side 621 that has embedded magnet(s) therein to allow a transparent shield 605 to be attached to the base plate 601 and a thin plate 623. The transparent shield 605 also includes embedded magnet(s) or metal (not shown) such that it can be removably attached to the base plate 601. A vacuum pipe 607 is positioned around a perimeter of the transparent shield 605. The vacuum pipe 607 includes a plurality of holes distributed randomly across its surface. For example, as shown in FIG. 6, holes 615 are more densely distributed along some parts of the vacuum pipe 607 while some parts of the vacuum pipe 607 only have a few sparsely distributed holes.

Figure 7A:
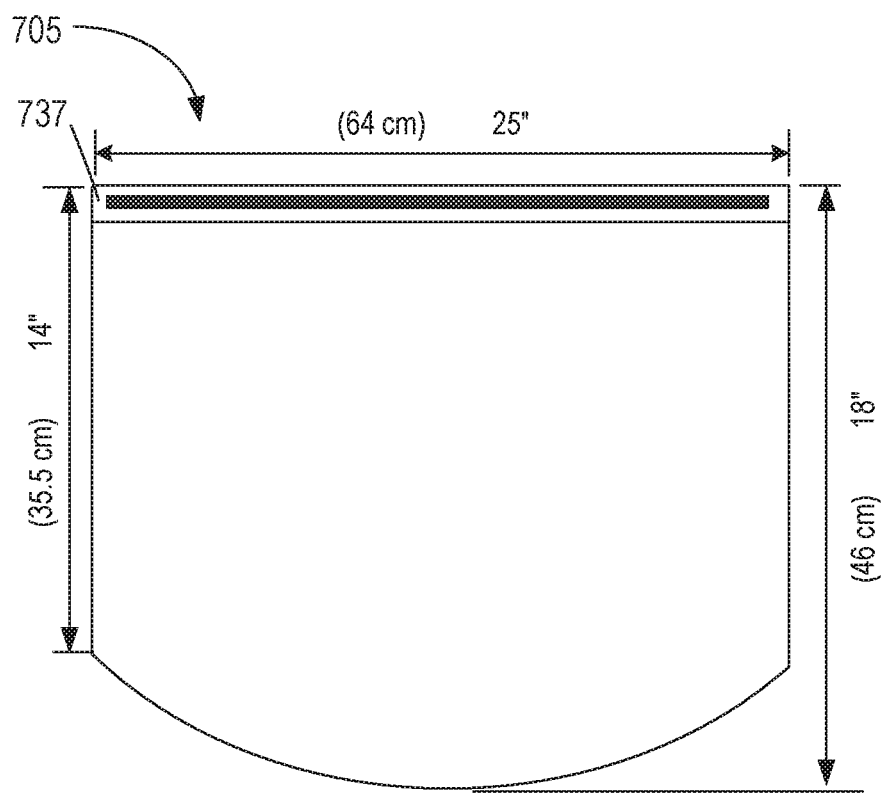
FIG. 7A illustrates a flat piece of transparent shield to be attached to a base plate of a protective shield system in accordance with one or more embodiments of the present technology.
Figure 7B:
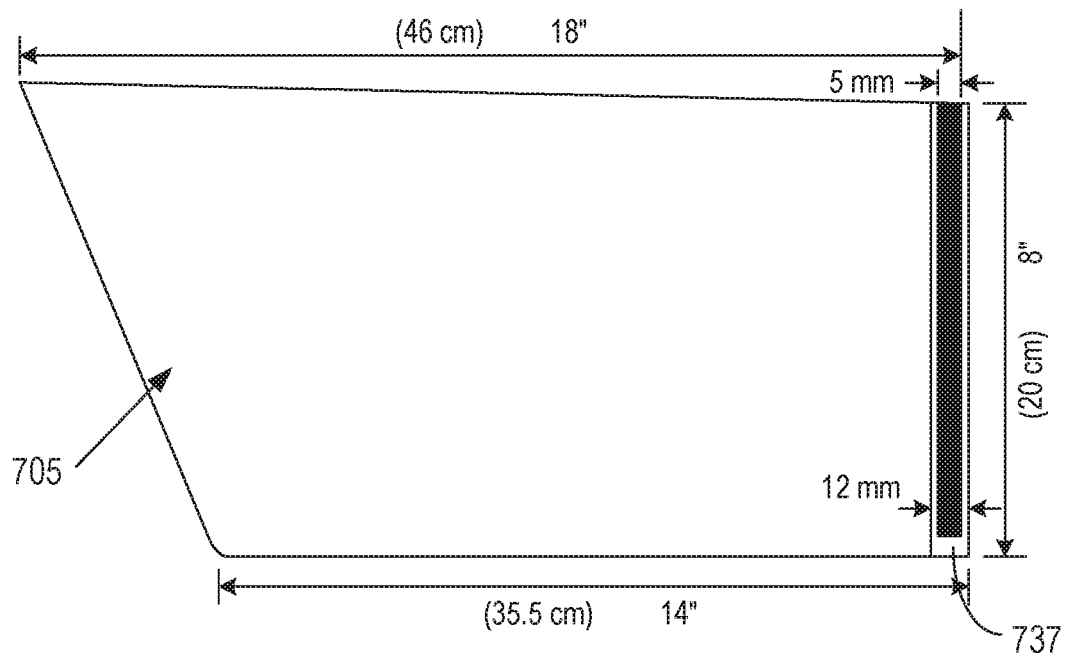
FIG. 7B illustrates a side view of a transparent shield that is bent into a curved position for attached to the base plate of the protective shield system in accordance with one or more embodiments of the present technology.
Figure 7C:
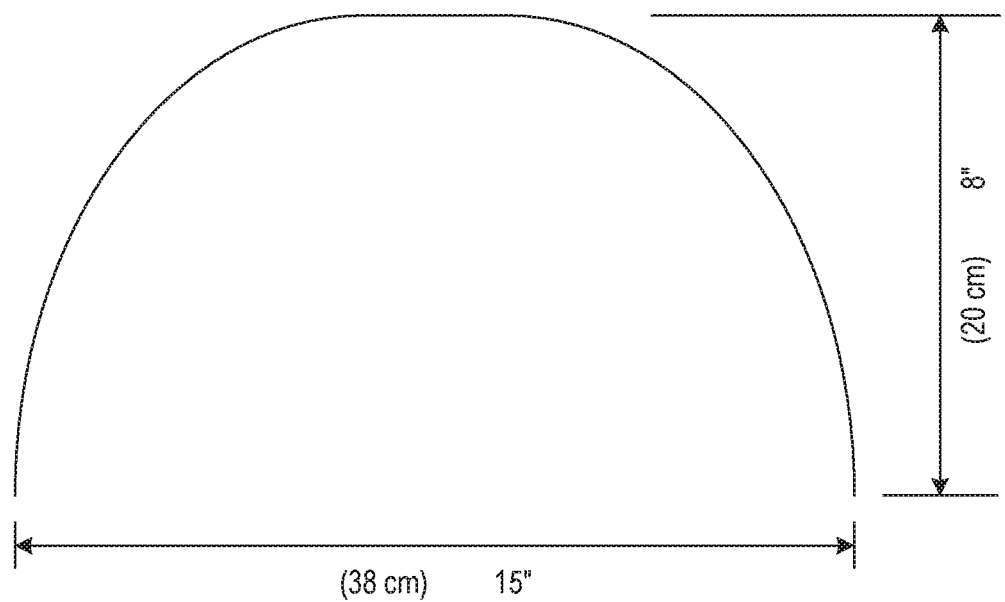
FIG. 7C illustrates a front view of the transparent shield shown in FIG. 7B in accordance with one or more embodiments of the present technology.

The dimension of the transparent shield can vary based on the requirements of the procedures, size of the patient, or the body part of interest. FIGS. 7A-7C illustrate example dimensions of a transparent shield that is suitable for a dental procedure in accordance with one or more embodiments of the present technology. FIG. 7A illustrates a flat piece of transparent shield 705 to be attached to a base plate of a protective shield system in accordance with one or more embodiments of the present technology. The transparent shield 705 includes a thick section 737 that has a piece of embedded metal to allow the transparent shield 705 to be attached to a base plate. The transparent shield 705 has a curved side to provide optimal protection to the healthcare professional when it is bent. The width of the transparent shield 705 ranges from 50 to 100 cm, depending on the curvature of the base plate. A first length of the transparent shield 705 from the section that includes the embedded metal to the farthest point of the curved side ranges from 15 to 25 inches (or from 38 to 64 cm). A second length of transparent shield 705 from the section that includes the embedded metal to the closest point of the curved side ranges from 10 to 15 inches (or from 25 to 38 cm). For example, in FIG. 7A, the width of the transparent shield 705 is 25 inches (or around 64 cm). The first length of the transparent shield 705 is 18 inches (or around 46 cm) and the second length of the transparent shield 705 is 14 inches (or around 35.5 cm). In some implementations, shields with different dimensions may be used for adults versus children versus infants.

FIGS. 7B-7C illustrate side and front views of a transparent shield 705 that is bent into a curved position for attached to the base plate of the protective shield system. The bent transparent shield 705 has a side profile similar to a trapezoid, such as shown in FIG. 7B. The height of the bent transparent shield 705, that is, the radius or height of a semi-circle shaped base plate, ranges, in some implementations, from 15 to 25 cm (e.g., 20 cm as shown in FIGS. 7B-7C). The bent transparent shield 705 has a width that can be fitted to a base plate, which, in some implementations, has a width ranges from 10 to 25 inches (or around 25 to 65 cm) depending on the type of procedure to be performed. In the example shown in FIG. 7C, the bent transparent shield 705 has a width of 15 inches (or 38 cm).

Figure 8:
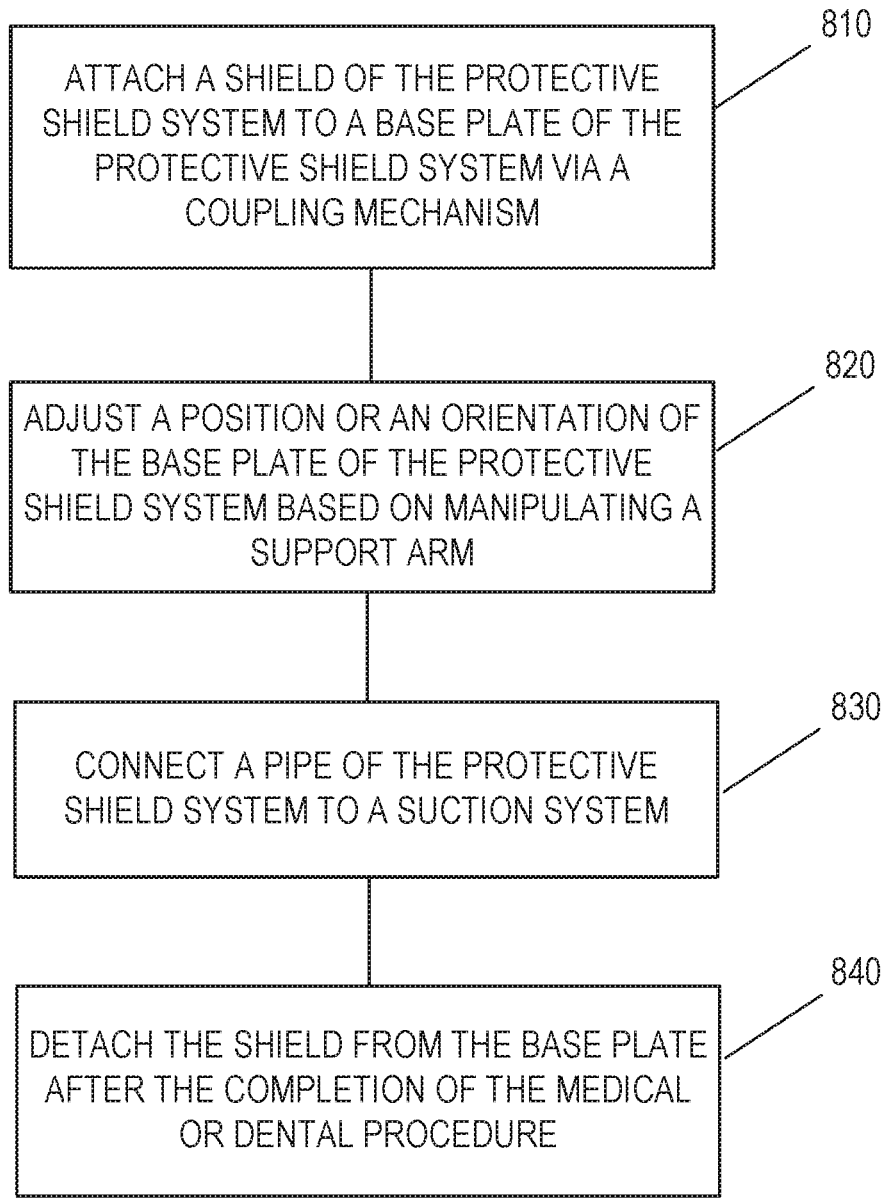
FIG. 8 is a flowchart representation of a method for performing a medical or dental procedure in accordance with one or more embodiments of the present technology.

FIG. 8 is a flowchart representation of a method 800 for performing a medical or dental procedure in accordance with one or more embodiments of the present technology. The method 800 includes, at operation 810, attaching a shield of the protective shield system to a base plate of the protective shield system via a coupling mechanism. The method 800 includes, at operation 820, adjusting a position or an orientation of the base plate of the protective shield system based on manipulating a support arm. A first end of the support arm is connected to the base plate and a second end of the support arm is affixed to on section of an operating platform. The method 800 includes, at operation 830, connecting a pipe of the protective shield system to a suction system. The pipe is positioned around a perimeter of the transparent shield and comprises a plurality of holes configured to remove, via the suction system, aerosol droplets or condensation of the aerosol droplets from below the transparent shield. The method 800 also includes, at operation 840, detaching the shield from the base plate after the completion of the medical or dental procedure.

In some embodiments, the coupling mechanism comprises one or more magnets embedded in the base plate and a magnet or a metal component embedded in an end section of the shield. Attaching the shield comprises bringing the end of the shield having the magnet or the metal component embedded therein in proximity to the one or more magnets embedded in the base plate until the shield is pulled toward the base plate via a magnetic force. In some embodiments, the coupling mechanism comprises a groove on the base plate and wherein attaching the shield comprises sliding the shield into the groove until an end of the groove is in contact with the base plate. In some embodiments, adjusting a position or an orientation of the base plate comprises moving or rotating multiple sections of the support arm independently with respect to each other to position the shield at a first position.

In some embodiments, the method includes sanitizing the base plate of the protective shield system. In some embodiments, the method includes selecting, prior to performing the medical or dental procedure, a size of the base plate based on: a type of the medical or dental procedure, or an age of a patient.

In one example aspect, a protective shield system for reducing transmission of aerosolized particles in a medical or dental procedure is disclosed. The protective shield system includes a base plate, a shield having at least one transparent section, and a pipe or conduit comprising a plurality of holes thereon. The shield is configured to be removably attached to the base plate so as to allow attachment of the shield to the base plate prior to the medical or dental procedure and removal of the shield from the base plate after the medical or dental procedure. The pipe or conduit is positioned adjacent to an inner surface of the shield and on at least part of a perimeter of the shield. The pipe includes an end that is configured to connect to a suction system to enable removal of the aerosolized particles from below the shield during the medical or dental procedure.

In some embodiments, the system includes a support arm. A first end of the support arm is coupled to the base plate to enable an adjustment of a position or an orientation of the base plate and a second end of the support arm is connected to an operating platform. In some embodiments, the support arm comprises a flexible arm and the operating platform is a dental chair. In some embodiments, the system further includes a rotating joint. A first section of the rotating joint is affixed to the first end of the flexible arm and a second section of the rotating joint is positioned at the base plate to enable the base plate and the flexible arm to be rotatably connected together. In some embodiments, the support arm comprises multiple sections configured to move or rotate independently with respect to each other.

In some embodiments, the base plate comprises one or more magnets embedded within the base plate. The shield comprises one or more magnets, or one or more metallic components, at an end thereof to allow the shield to be removably attached to the one or more magnets of the base plate. In some embodiments, the base plate comprises a first section and a second section, the first section being thicker than the second section. The one or more magnets are embedded within the first section of the base plate. In some embodiments, the base plate comprises a groove configured to allow the shield to slide in place and be attached to the base plate.

In some embodiments, the base plate comprises an interface through which the pipe or conduit is connected to the suction system. In some embodiments, the pipe or conduit is positioned to be in contact with the shield. In some embodiments, the system further includes a padding positioned between the pipe and the shield. The padding is in contact with both the pipe and the shield to prevent leakage of the aerosolized particles.

In some embodiments, the plurality of holes is distributed uniformly across a surface of the pipe or conduit. In some embodiments, the plurality of holes is distributed non-uniformly across a surface of the pipe or conduit. In some embodiments, the plurality of holes has a regular or irregular shape. In some embodiments, at least some of the plurality of the holes are positioned to face toward an inner surface of the shield to allow removal of condensation from the inner surface of the shield.

In some embodiments, the shield is fully transparent. In some embodiments, the shield includes one or more transparent sections to allow a clear line of sight to a portion of a patient's face.

In some embodiments, a dimension of the base plate is selected based on a type of the medical or dental procedure, or an age of a patient. In some embodiments, the base plate has a height that ranges from 15 to 25 cm and a width that ranges from 25 to 65 cm.

In some embodiments, the protective shield system further comprises the suction system, wherein the suction system is configured to produce multiple levels of suction strengths. In some embodiments, the pipe or a conduit has one of a circular or rectangular cross-section. In some embodiments, the base plate is formed as a hard-plastic component. In some embodiments, the shield, upon attachment to the base plate, is configured to move in three dimensions. In some embodiments, the base plate is coupled to a support arm by a ball-and-socket joint.

It will be appreciated that the disclosed protective shield system can provide a higher level of protection for healthcare personnel against communicable diseases. The transparent shield allows a healthcare professional to clearly view the operating area during a medical or dental procedure while preventing aerosol droplets or mists from splashing onto the healthcare professional. The base plate that the transparent shield is attached to can be flexibly controlled before or during the procedure to ensure that there is sufficient room underneath the transparent shield to operate on the patient. Furthermore, the vacuum pipe in contact with the transparent shield is connected to a vacuum suction system to suck away any condensation of the droplets or mists on the transparent shield, thereby eliminating the possibility of the condensation dripping onto unprotected surfaces.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

The invention claimed is:

1. A protective shield system for reducing transmission of aerosolized particles in a medical or dental procedure, comprising:
   a base plate that is flat and has a curved edge;
   a shield having at least one transparent section, the shield configured to be removably attached to the base plate so as to allow attachment of the shield to the base plate prior to the medical or dental procedure and removal of the shield from the base plate after the medical or dental procedure, wherein, when in an attached configuration, one end of the shield is attached to the curved edge of the base plate and an opposite end of the shield is unattached, and wherein, when in the attached configuration, the shield forms a curved surface that includes the at least one transparent section and forms a space bounded by the curved surface configured to allow access to a patient for preforming the medical or dental procedure,
   a pipe attached to, and in contact with, the shield and comprising a plurality of holes, the pipe positioned on at least part of a perimeter of the opposite end of the shield and including an end that is configured to connect to a suction system to enable removal of the aerosolized particles from the space bounded by the curved surface during the medical or dental procedure; and
   a support arm coupled to the base plate to hold the base plate in position and to enable an adjustment of a position or an orientation of the base plate such that the shield is configured to at least cover oral and nasal cavities of the patient.

2. The system of claim 1,
   wherein a first end of the support arm is coupled to the base plate to enable the adjustment of the position or the orientation of the base plate and a second end of the support arm is connected to an operating platform.

3. The system of claim 2, wherein the support arm comprises a flexible arm and the operating platform is a dental chair.

4. The system of claim 3, further comprising a rotating joint, wherein a first section of the rotating joint is affixed to the first end of the flexible arm and a second section of the rotating joint is positioned at the base plate to enable the base plate and the flexible arm to be rotatably connected together.

5. The system of claim 1, wherein the support arm comprises multiple sections configured to move or rotate independently with respect to each other.

6. The system of claim 1, wherein the base plate comprises one or more magnets embedded within the base plate, and wherein the shield comprises one or more magnets, or one or more metallic components, at an end thereof to allow the shield to be removably attached to the one or more magnets of the base plate.

7. The system of claim 6, wherein the base plate comprises a first section and a second section, the first section being thicker than the second section, and wherein the one or more magnets are embedded within the first section of the base plate.

8. The system of claim 1, wherein the base plate comprises a groove configured to allow the shield to be attached to the base plate.

9. The system of claim 1, wherein the base plate comprises an interface through which the pipe is connected to the suction system.

10. The system of claim 1, further comprising a padding positioned between the pipe and the shield, the padding being in contact with both the pipe and the shield to prevent leakage of the aerosolized particles.

11. The system of claim 1, wherein the plurality of holes are distributed uniformly across a surface of the pipe.

12. The system of claim 1, wherein the plurality of holes are distributed non-uniformly across a surface of the pipe.

13. The system of claim 1, wherein each of the plurality of holes has a regular or irregular shape.

14. The system of claim 1, wherein at least some of the plurality of the holes are positioned to face toward the curved surface of the shield to allow removal of condensation from the curved surface of the shield.

15. The system of claim 1, wherein the shield is fully transparent.

16. The system of claim 1, wherein one or more of the at least one transparent sections are configured to allow a clear line of sight to the oral and nasal cavities of the patient.

17. The system of claim 1, wherein a dimension of the base plate is selected based on a type of the medical or dental procedure, or an age of a patient.

18. The system of claim 17, wherein the base plate has a height that ranges from 15 to 25 cm and a width that ranges from 25 to 65 cm.

19. The system of claim 1, comprising the suction system, wherein the suction system is configured to produce multiple levels of suction strengths.

20. The system of claim 1, wherein the pipe has one of a circular or rectangular cross-section.

21. The system of claim 1, wherein the base plate is formed as a hard-plastic component.

22. The system of claim 1, wherein the shield, upon attachment to the base plate, is configured to move in three dimensions.

23. The system of claim 1, wherein the base plate is coupled to a support arm by a ball-and-socket joint.

24. The system of claim 1, wherein one or both of the pipe or the shield are disposable.

25. A method for performing a medical or dental procedure, comprising:

attaching a shield of a protective shield system to a base plate of the protective shield system via a coupling mechanism, wherein the base plate is flat and has a curved edge, wherein the shield has at least one transparent section, and wherein, when in an attached configuration, one end of the shield is attached to the curved edge of the base plate and an opposite end of the shield is unattached, and wherein, when in the attached configuration, the shield forms a curved surface that includes the at least one transparent section and forms a space bounded by the curved surface configured to allow access to a patient for preforming the medical or dental procedure, adjusting a position or an orientation of the base plate of the protective shield system based on manipulating a support arm such that the shield is configured to at least cover oral and nasal cavities of the patient, wherein a first end of the support arm is connected to the base plate and a second end of the support arm is affixed to on section of an operating platform;

connecting a pipe of the protective shield system to a suction system, wherein the pipe is attached to and is in contact with the shield and positioned around a perimeter of the opposite end of the shield, the pipe comprising a plurality of holes configured to remove, via the suction system, aerosol droplets or condensation of the aerosol droplets from the space bounded by the curved surface; and detaching the shield from the base plate after the completion of the medical or dental procedure.

26. The method of claim 25, wherein the coupling mechanism comprises one or more magnets embedded in the base plate and a magnet or a metal component embedded in an end section of the shield, and wherein attaching the shield comprises bringing the end of the shield having the magnet or the metal component embedded therein in proximity to the one or more magnets embedded in the base plate until the shield is pulled toward the base plate via a magnetic force.

27. The method of claim 25, wherein adjusting the position or the orientation of the base plate comprises:

moving or rotating multiple sections of the support arm independently with respect to each other to position the shield at a first position.

28. The method of claim 25, further comprising:

sanitizing the base plate of the protective shield system.

29. The method of claim 25, comprising:

selecting, prior to performing the medical or dental procedure, a size of the base plate based on: a type of the medical or dental procedure, or an age of a patient.

* * * * *